United States Patent [19]

Quinn et al.

[11] Patent Number: 4,981,471
[45] Date of Patent: * Jan. 1, 1991

[54] DEVICE FOR INTUBATION OF PERCUTANEOUS ENDOSCOPIC OSTOMY

[75] Inventors: David G. Quinn, Grayslake; Robert B. Edwards, II, Libertyville; Erik Andersen, Vernon Hills, all of Ill.

[73] Assignee: Corpak, Inc., Wheeling, Ill.

[*] Notice: The portion of the term of this patent subsequent to Jan. 3, 2006 has been disclaimed.

[21] Appl. No.: 352,092

[22] Filed: May 15, 1989

Related U.S. Application Data

[63] Continuation-in-part of Ser. No. 291,115, Dec. 28, 1988, Pat. No. 4,900,306, which is a continuation-in-part of Ser. No. 144,527, Jan. 15, 1988, Pat. No. 4,795,430.

[51] Int. Cl.$^5$ .............................................. A61M 29/02
[52] U.S. Cl. ............................................ 604/97; 128/6
[58] Field of Search ................. 604/96, 97, 98, 99; 128/4, 6

[56] References Cited

U.S. PATENT DOCUMENTS

| | | | |
|---|---|---|---|
| 3,190,291 | 6/1965 | Foley | 604/98 |
| 4,141,364 | 2/1979 | Schultze | 128/4 X |
| 4,356,824 | 11/1982 | Vazquez | 604/98 X |
| 4,795,430 | 1/1989 | Quinn et al. | 604/97 |
| 4,900,306 | 2/1990 | Quinn et al. | 604/97 |

FOREIGN PATENT DOCUMENTS

3444909 12/1984 Fed. Rep. of Germany.
8705894  4/1987 Fed. Rep. of Germany.

*Primary Examiner*—William H. Grieb
*Attorney, Agent, or Firm*—Wallenstein, Wagner & Hattis, Ltd.

[57] ABSTRACT

A device for intubating an ostomy, formed by a percutaneous endoscopic technique including a multi-lumen tube, having at least a fluid delivery lumen and an inflation lumen. The tube includes a port near one end to dispose the inflation lumen to ambient air and an outlet at an other end to convey fluid from within the fluid lumen into a patient. An inflatable member, is joined near the other end of the tube and is inflatable and deflatable through the inflation lumen. In a deflated state, the member assumes an edge-free outer configuration to facilitate intubation of the device into the patient. In a fully inflated state, the member assumes an outer configuration defining an edged, generally flat surface to more diffusely contact and abut against inner tissue surfaces surrounding the gastrostomy. Joined to the one end of the tube is an elongated tapered sleeve which encloses the one end of the tube. The tapered end of the sleeve carries a suture loop for use in intubating the device. The tube seals the ambient air port through use of a pressure responsive skirt portion disposed from the sleeve or through use of a frangible plug. Deflation of the member is accomplished by a unique deflation collar having a tapered passage. The inflatable member is drawn through the tapered passage.

13 Claims, 4 Drawing Sheets ns4,981,471

DEVICE FOR INTUBATION OF PERCUTANEOUS ENDOSCOPIC OSTOMY

REFERENCE TO A RELATED APPLICATION

This application is a continuation-in-part of co-pending U.S. patent application Ser. No. 291,115 filed Dec. 28, 1988 now U.S. Pat. No. 4,900,306, granted Feb. 13, 1990 which was a continuation-in-part of U.S. patent application Ser. No. 07/144,527 filed Jan. 15, 1988, now U.S. Pat. No. 4,795,430 granted Jan. 3, 1989.

DESCRIPTION

1. Technical Field of the Invention

The present invention generally relates to apparatuses utilized in a feeding tube gastrostomy and, in particular, to a device for intubating a gastrostomy or other ostomy formed by a percutaneous endoscopic technique.

2. Background of the Invention

A surgically formed gastrostomy is a preferred method for administering enteral nutrition when oral alimentation is not possible. However the placement and formation of a gastrostomy requires a laparotomy performed under general anesthesia. Such requirements are unacceptable, particularly in patients who present a high general anesthetic risk. Hence a percutaneous endoscopic technique was developed which may be performed under local anesthesia and requires no laparotomy. This technique is disclosed for example in Gauderer & Ponsky, "A Simplified Technique For Constructing A Tube Feeding Gastrostomy", Surgery, Gynecology & Obstetrics, vol. 152, 1/81, pp. 82–85, the teachings of which are incorporated herein by reference. In addition, a percutaneous endoscopic formation of a gastrostomy may be performed by a gastroenterologist rather than a surgeon.

Generally, in forming a gastrostomy using a percutaneous endoscopic technique, an illuminating fiberoptic endoscope is inserted into a patient's mouth and advanced into the stomach. The stomach is then inflated with room air and the positioning of the endoscope may be externally visualized by the illuminated tip of the endoscope. The abdominal and gastric walls are then pierced at the positioning of the endoscope and the gastroscope thereby formed.

In order to intubate the gastrostomy, one end of a suture thread is passed externally through the gastrostomy. The one end of the suture is snared by the endoscope and drawn upward through the stomach, esophagus and out of the mouth of the patient. The suture is then tied to the end of a specially prepared catheter. The catheter is typically a 12 to 20 Fr. Pezzer or mushroom-type catheter in which a tapered cannula has been secured to one end of the catheter. The tip of the cannula carries a length of suture to permit the catheter to be tied to the one end of the suture extending from the patient's mouth. A previously removed connecting end of the Pezzer catheter is placed over the catheter and positioned slightly above the mushroom tip of the catheter to function as one perpendicular bumper for retaining the intubated catheter within the gastrostomy.

The catheter is then intubated by pulling it in a retrograde manner through the mouth, esophagus and into the stomach until the perpendicular bumper above the mushroom tip abuts against inner surfaces of the gastrostomy and the gastric wall. A second perpendicular bumper is placed over the catheter and secured to the abdominal wall to form an anchoring structure of the type disclosed in FIG. 6 of the Gauderer & Ponsky reference cited above.

There are many problems with the prior art percutaneous endoscopic catheters. The first perpendicular bumper placed above the mushroom retention tip includes several edges which result in an uncomfortable and difficult intubation of the catheter. Preferably, the retention tip should be more pliable and have a contoured, edge-free outer configuration to promote a relatively comfortable intubation of the catheter.

In addition, the prior art perpendicular bumpers which abut against the gastric and abdominal walls exert concentrated, abrasive contact pressure on specific tissue areas. Such specific contact has been found to create necrosis of the affected tissue. Hence, a need arose for an anchoring system for the retention tip of the intubated catheter which would evenly diffuse retention pressure on the surrounding affected tissue to avoid tissue necrosis.

Further, the inner perpendicular anchoring bumper in some cases would pull free and in most cases was difficult to remove upon conclusion of enteral feeding therapy. Removal is now achieved either by physically pulling the retention tip through the gastrostomy or allowing the tip to pass freely through the gastroenteral tract to become excreted. Either alternative is uncomfortable for the patient and subject to complications. Hence, a need arose for an anchoring and retention tip which could be easily and comfortably removed at the conclusion of enteral feeding therapy through the gastrostomy.

Prior to the development of the present invention, a need existed for a catheter specially designed for intubating a gastrostomy or an other ostomy formed by a percutaneous endoscopic technique having (1) an enlarged retention member which is pliable and smoothly contoured for a more comfortable intubation, (2) anchor means which more evenly distributes contact surrounding tissues thereby avoiding tissue necrosis, (3) anchor means which remain abutted against tissue surrounding the ostomy without pulling free and, (4) an anchor means and retention member which may be compressed or collapsed to facilitate removal of the tube externally through the gastrostomy itself upon completion of enteral feeding therapy. Preferably, unlike the prior art retention tip and bumpers, a most efficient catheter design would combine the anchor means and retention member into a single structure.

SUMMARY OF THE INVENTION

According to the present invention, a specially designed device has been developed for intubating an ostomy, as for example, a gastrostomy, formed by a percutaneous endoscopic technique. The device of the present inventions meets the foregoing described needs by employing a multi-lumen enteral feeding tube, preferably having at least a fluid delivery lumen and an inflation lumen. The tube includes a port near one end to dispose the inflation lumen to ambient air and an outlet at an other end to convey fluid from within the fluid lumen into the patient. A retention member, preferably an inflatable cuff or a pre-distended balloon, is joined near the other end of the tube. The retention member is in communication with the inflation lumen and is inflatable and deflatable through the inflation lumen.

The cuff is substantially filled with a resilient porous material for maintaining the walls of the member in a fully inflated position. The pre-distended balloon is devoid of such resilient material. The walls of both the cuff or balloon are designed so that in a deflated state, each assumes an edge-free, preferably rounded, outer configuration to facilitate intubation of the device into the patient. Likewise, in a fully inflated state, the cuff or balloon assumes an outer configuration defining a surface to more diffusely contact and abut against the inner tissue surfaces surrounding the gastrostomy.

Joined to the one end of the tube is an elongated tapered sleeve which encloses the one end of the tube. The tapered end of the sleeve carries, preferably, a suture loop or loop of nylon-coated stranded wire for use in intubating the device.

In all embodiments of the present invention, means are provided for sealing the inflation lumen. For example, in one embodiment, the sleeve includes a skirt portion which creates a circumferential air tight seal about the exterior of the tube to selectively seal the ambient air port. The skirt portion of the sleeve is air pressure responsive to permit escape of air from the inflation lumen through the port but preventing the ingress of air into the inflation lumen through the port.

In an alternate embodiment, the ambient air port is sealed by a frangible plug member. The frangible plug member generally includes a stem frangibly connected to an enlarged gripping portion.

The device of the present invention is utilized in intubating a gastrostomy formed by a percutaneous endoscopic technique by the following steps. First, prior to intubation of the device into a patient, the retention member is deflated by compressing it, thereby expelling air out of the inflation lumen through the port. In one embodiment, the skirt portion of the sleeve expands outwardly in response to the greater air pressure within the lumen to permit the escape of air out of the inflation lumen through the port. Upon fully deflating the retention member, the air pressure within the inflation lumen decreases relative to ambient air pressure such that the skirt portion contracts inwardly to seal the ambient air port thus preventing ingress of air into the inflation lumen.

In the alternate embodiment, the ambient air port may be sealed by inserting the stem of the frangible plug member into the port. The stem is inserted into the inflation lumen to a point such that when the frangible connection between the stem portion is broken, the stem remains in the port to occlude the inflation lumen.

Initial deflation of the retention member may be accomplished by manually squeezing the member. This, however, increases the risk of microbial contamination. For purposes of aseptic procedure, it is preferable to deflate the member with a deflation device which prevents direct human contact with the member. In one embodiment, the present invention provides for initial deflation of the member through use of a deflation strap. The member is captured within the deflation strap and the strap is then tightened thus deflating the member and maintaining it in a deflated position until the ambient art port is sealed. In another embodiment a deflation collar is provided for deflating the member. The deflation collar has a tapered passage interconnecting a relatively large opening at one end of the collar to a relatively small opening at its opposite end. The member is deflated by drawing it through the collar from the large opening to the small opening thus compressing the member. The deflation strap and the deflation collar are particularly useful in the embodiment of the present invention wherein a frangible plug is utilized for initial sealing of the inflation lumen.

Sealing of the ambient air port prevents re-inflation of the member. In a deflated state, the retention member assumes an edge free generally oval outer configuration.

Upon deflating the member and sealing the ambient air port, the suture loop carried on the tapered end of the sleeve is tied to the one end of the suture which extends from the patient's mouth. The gastroenterologist then begins pulling on the other end of the suture extending externally from the gastrostomy to lead the device in a retrograde manner through the mouth, esophagus and ultimately into the stomach. The retrograde drawing of the device continues until the deflated member abuts against inner tissue surfaces surrounding the gastrostomy. Air is then externally introduced into the inflation lumen to re-inflate the retention member to change the outer configuration of the member to create a generally flat anchor surface.

In the one method of practicing the present invention, re-inflation of the member may be achieved by severing the multi-lumen tube below the sleeve to remove the sleeve from the tube. This exposes the inflation lumen to ambient air resulting in re-inflation of the member. In the alternate method wherein a frangible plug has occluded the inflation lumen, the multi-lumen tube may be similarly severed below the plugged area of the inflation lumen.

After re-inflation of the member, the inflation lumen should be sealed with a plug, such as another frangible plug member, or other device to prevent deflation of the retention member. Then, as is conventional, the severed end of the multi-lumen tube is secured at the exterior of the ostomy by means known in the art such as by tape or suture. This prevents the inflated member from dislodging from the tissue wall and to keep the member urged against the inner tissue surface surrounding the ostomy.

A luer adaptor or other tube connecting device may be affixed to the severed end of the tube to place the tube in fluid communication with an enteral nutritional fluid source.

Other advantages and aspects of the invention will become apparent upon making reference to the specification, claims, and drawings to follow.

DETAILED DESCRIPTION OF THE INVENTION

While this invention is susceptible of embodiment in many different forms, there is shown in the drawings and will herein be described in detail at least two embodiments of the invention. The present disclosure is to be considered as an exemplification of the principles of the invention and is not intended to limit the broad aspect of the invention to embodiment illustrated.

Figure 1:
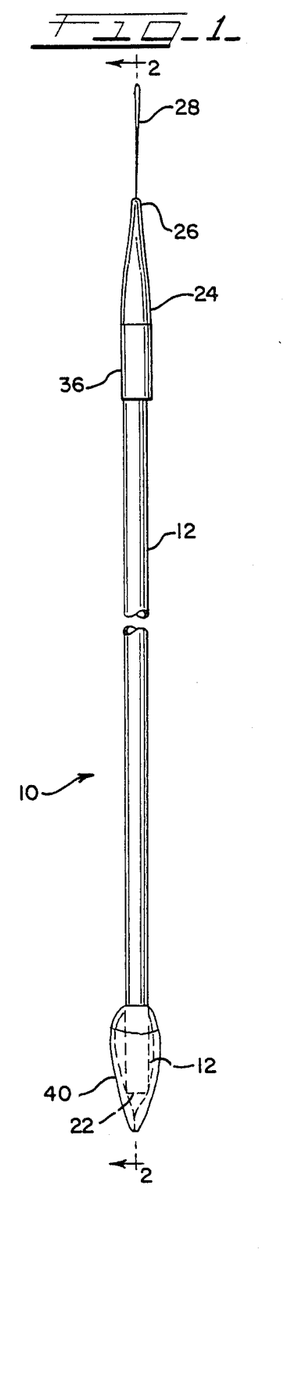
FIG. 1 discloses in perspective view one embodiment of the present invention.
Figures 4, 5, 6, 6A:
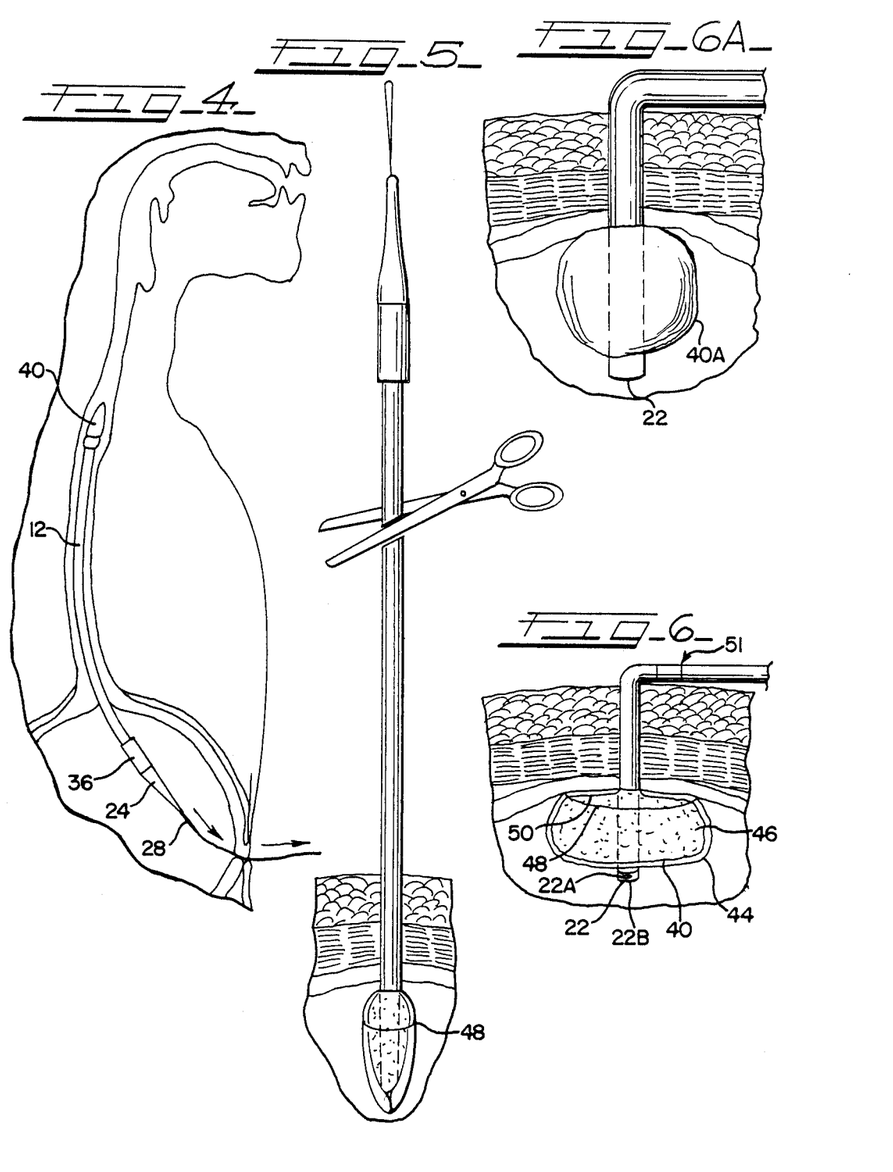
FIG. 4 illustrates retrograde intubation of one embodiment of the device of the present invention.
FIG. 5 illustrates severing a portion of the tube of the present invention to introduce air into the inflation lumen.
FIG. 6 discloses a foam-filled cuff embodiment of the retention member of the present invention.
FIG. 6A discloses a pre-distended balloon embodiment of the retention member of the present invention.

Referring now to the drawings, FIG. 1 discloses one embodiment of device 10 of the present invention comprised of a multi-lumen enteral feeding tube. As disclosed in FIG. 2 and best disclosed in FIG. 2A, feeding tube 12 includes at least an inflation lumen 14 and a fluid delivery lumen 16. Lumens 14 and 16 are separated by a septum 18. As disclosed in FIG. 2, one end 12A of tube 12 has at least one ambient air port 20 which, as will be disclosed later in greater detail, disposes inflation lumen 14 in communication with ambient air. At an other end 12B of tube 12, the fluid outlet 22 (shown in phantom in FIG. 2) conveys fluid from fluid lumen 16 into a patient. As shown in FIG. 6, outlet 22 embodies a tapered polyurethane cap having at least one side inlet 22A and an axial inlet 22B. A tapered cap both conceals any abrasive edges on outlet 22 and facilitates fluid flow.

Sealably secured to end 12A of tube 12 is an enclosed sleeve 24, preferably having a tapered elongated conical terminal end 26. The tapered conical outer configuration of terminal end 26 permits a traumatic parting of esophageal and gastric tissues during the intubation process. As disclosed in FIGS. 1 and 2 disposed on the terminal end 26 of sleeve 24 is a loop 28 which permits device 10 to be tied to the end of the suture extending from the patient's mouth during the percutaneous endoscopic technique (not shown in the drawings). Loop 28 may either be a length of surgical suture or nylon-coated stranded wire insert molded into terminal end 26. As disclosed in FIG. 2, loop 28 may preferably fully extend through sleeve 24 through a channel 32 and be secured to end 12A of tube 12 by a fastening knot or other fastening device 34 secured to the septum 18.

FIGS. 1 through 3A disclose one preferred embodiment of the present invention wherein, joined to sleeve 24, is a skirt portion 36 which circumferentially surrounds and 12A of tube 12 in such a manner to create an airtight seal between skirt portion 36 and outer surfaces of end 12A. Skirt portion 36 is made from a highly pliable plastic or latex rubber so as to be air pressure responsive permitting selective sealing of ambient air port 20. Specifically, skirt portion 36 responds to greater air pressure within inflation lumen 14 to permit the escape of air out of lumen 14 through port 20 However, when ambient air pressure exceeds the air pressure within lumen 14, then skirt portion 36 contracts inwardly to seal port 20 to prevent the further ingress of air into lumen 14.

Figures 2, 2A, 3, 3A:
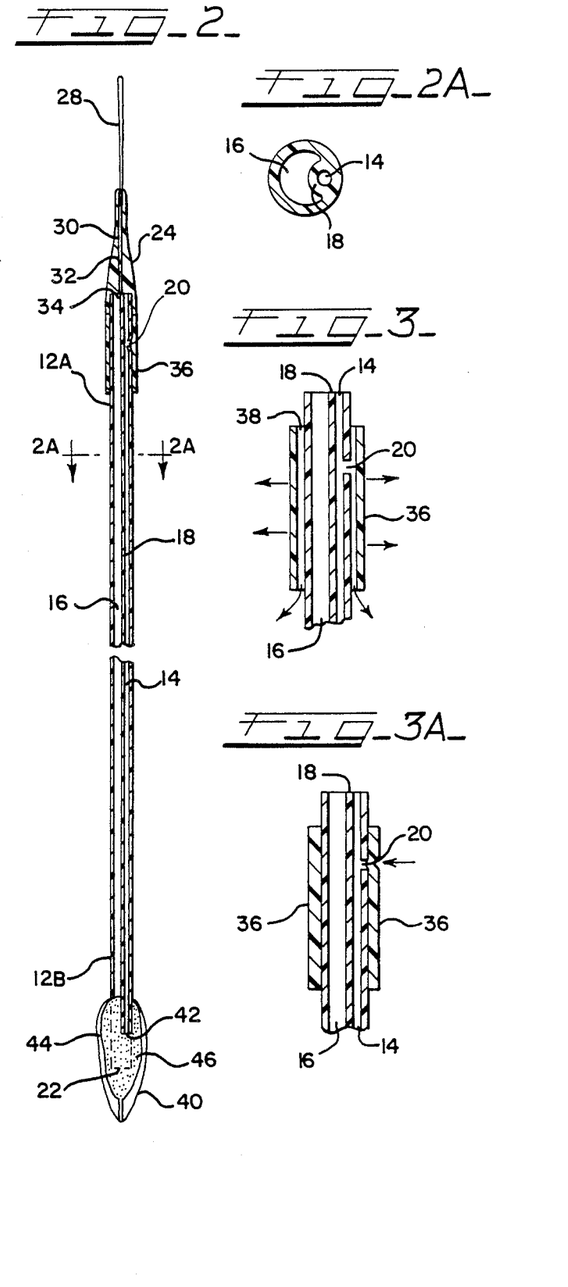
FIG. 2 is a longitudinal section taken along line 2—2 in FIG. 1.
FIG. 2A is a vertical section taken through line 2A—2A of FIG. 2.
FIG. 3 is a fragmented detailed view of a portion of FIG. 2 disclosing outward flexing of the skirt portion of the elongated sleeve permitting an escape of air from within the inflation lumen.
FIG. 3A is the same view of FIG. 3 disclosing an inward contraction of the skirt portion to seal the ambient air port of the inflation lumen.

FIGS. 3 and 3A disclose in greater detail the selective sealing or diaphragmatic action of skirt portion 36. As disclosed in FIG. 3, when air pressure within inflation lumen 14 increases to exceed ambient air pressure, skirt 36 expands outwardly away from the walls of tube 12 to define a circumferential gap 38 which permits air to exit ambient port 20 and escape from under skirt portion 36. As disclosed in FIG. 3A, when ambient air pressure exceeds the air pressure within inflation lumen 14, skirt portion 36 contracts circumferentially about tube 12 closing gap 38 and thereby forming an airtight seal about tube 12 and port 20.

The selective sealing of ambient port 20 allows for the controlled inflation and deflation of a retention/anchor member 40 which preferably is embodied as an annular member or pre-distended balloon. As best disclosed in FIG. 2, retention member 40 is affixed to the other end 12B of tube 12. Retention member 40 is sealed and in gas communication with inflation lumen 14 through a terminal opening 42 in tube 12. As shown in phantom in FIG. 1 and 2, tube 12 passes through member 40 so that, as disclosed in FIG. 6, fluid outlet 22 extends below member 40.

FIG. 6 discloses one embodiment of retention member 40 embodying a cuff comprised of an outer wall 44 which defines a cavity preferably substantially filled with a porous resilient foam material 46. As disclosed in FIG. 6, foam material 46 is cut in a configuration so that when the member 40 is in a fully expanded position, foam material 46 maintains walls 44 in expanded position.

FIG. 6A discloses an alternative embodiment of retention member 40 embodied as a pre-distended balloon 40A. Unlike the cuff embodiment disclosed in FIG. 6, balloon 40A is void of a resilient foam material. Rather, balloon 40A is molded into a pre-distended condition. Specifically, balloon 40A is formed into an outer configuration representing a fully inflated state. As a result, balloon 40A readily assumes a full inflation configuration even where less than full inflation air pressure is introduced. Upon full deflation, balloon 40A collapses into a smaller outer configuration than the foam-filled cuff embodiment of retention member 40.

Retention member 40 is placed in a deflated state by compressing, preferably by squeezing, member 40 so that the air trapped within walls 44 and foam material 46 is expelled upwardly into the inflation lumen and out of port 20. Discontinuing such squeezing of member 40 results in a decrease in air pressure within inflation lumen 14 so that ambient air pressure acts upon skirt 36 to seal port 20 in the manner described above. Such sealing of port 20 prevents re-inflation of retention member 40 and maintains member 40 in a deflated position. Re-inflation of member 40 is achieved by introducing ambient air into inflation lumen 14 by methods to be described below in greater detail.

Member 40 combines in a single structure both the retention and anchoring functions achieved by prior art catheter mushroom-type tips and perpendicular rubber bumpers. However, unlike the prior art mushroom tip/bumper combination, member 40 in a deflated state, assumes an essentially edge-free, rounded configuration which facilitates intubation of device 10. Member 40, in a deflated state, preferably assumes a oval or pill-shape as disclosed in FIGS. 1 and 2. In a fully inflated state, member 40 assumes a different configuration. The walls 44 of member 40 are molded or pre-formed so that the outer configuration of member 40 changes from a deflated state to a fully inflated state. For example, member 40, when embodied as either a foam-filled cuff or a pre-distended balloon, may include a fold or crease line 48 which changes the outer configuration of member 40 from deflation to full inflation. As disclosed in FIG. 6, upon full inflation of member 40, fold line 48 defines a peripheral edge of a generally flat retention and anchor surface 50. Surface 50 is of a sufficient surface area to evenly distribute contact pressures on the tissue surrounding the gastrostomy to avoid the necrosis of tissue commonly encountered by use of prior art retention bumpers. Hence, a novel aspect of the present invention is that the retention member, in a deflated position, has an edge-free contour to facilitate a comfortable intubation, whereas, in a fully inflated state, retention member 40 assumes a different configuration to define an edged, flattened surface for anchoring tube 12 within the gastrostomy.

FIGS. 4 through 6 disclose the general method of using device 10 in intubating an ostomy formed by a percutaneous endoscopic technique. As disclosed in FIG. 4, after the length of suture has been drawn out of a patient's mouth such that the free ends of the suture extend from both the patient's mouth and the gastrostomy, the suture is tied to loop 28 of the device of the present invention. The device of the present invention is then drawn downward through the mouth, esophagus and into the stomach in a retrograde manner. The pulling of the suture through the gastrostomy continues until the deflated retention member 40 abuts against the inner tissue surfaces of the gastrostomy as disclosed in FIG. 5. To retain and anchor the fluid outlet end 12B of tube 12 within the gastrostomy, retention member 40 is reinflated by introducing air into the inflation lumen 14 and then the inflation lumen 14 is sealed as disclosed below to prevent inadvertent deflation. As is conventional, the exposed portion of tube 12 is then secured near the external tissue surface of the ostomy to maintain the position of the retention member 40 against the inner tissue surrounding the ostomy, as disclosed in FIG. 6. The exposed portion may be secured by conventional means such as by tape or suture 51 the tube 12 to the external tissue.

In one preferred method of using the present invention, re-inflation of the retention member 40 may be accomplished by severing, as disclosed in FIG. 5, completely through a portion of tube 12 external to the gastrostomy. Upon severing completely through tube 12, inflation lumen 14 is exposed to ambient air thereby raising the air pressure within lumen 14 to automatically inflate member 40. In some instances it may be necessary to assist the inflation operation by injecting air into inflation lumen 14 through the insertion of the tip of an air-filled syringe into inflation lumen 14. Upon full inflation of retention member 40, inflation lumen 14 is sealed with a plug or other device to prevent deflation of member 40, such as frangible plug 60 of FIG. 8 which will be disclosed in more detail below.

With retention and anchoring of device 10 complete, a luer adaptor or other tube connection means may be affixed to the severed end of tube 12 to join tube 12 to a source of enteral nutritional fluid. It should be noted that such adaptor or tube connection means may also function to seal inflation lumen 14.

FIGS. 7 through 10 disclose another preferred embodiment of the present invention.

Figures 7, 7A, 8, 9, 10:
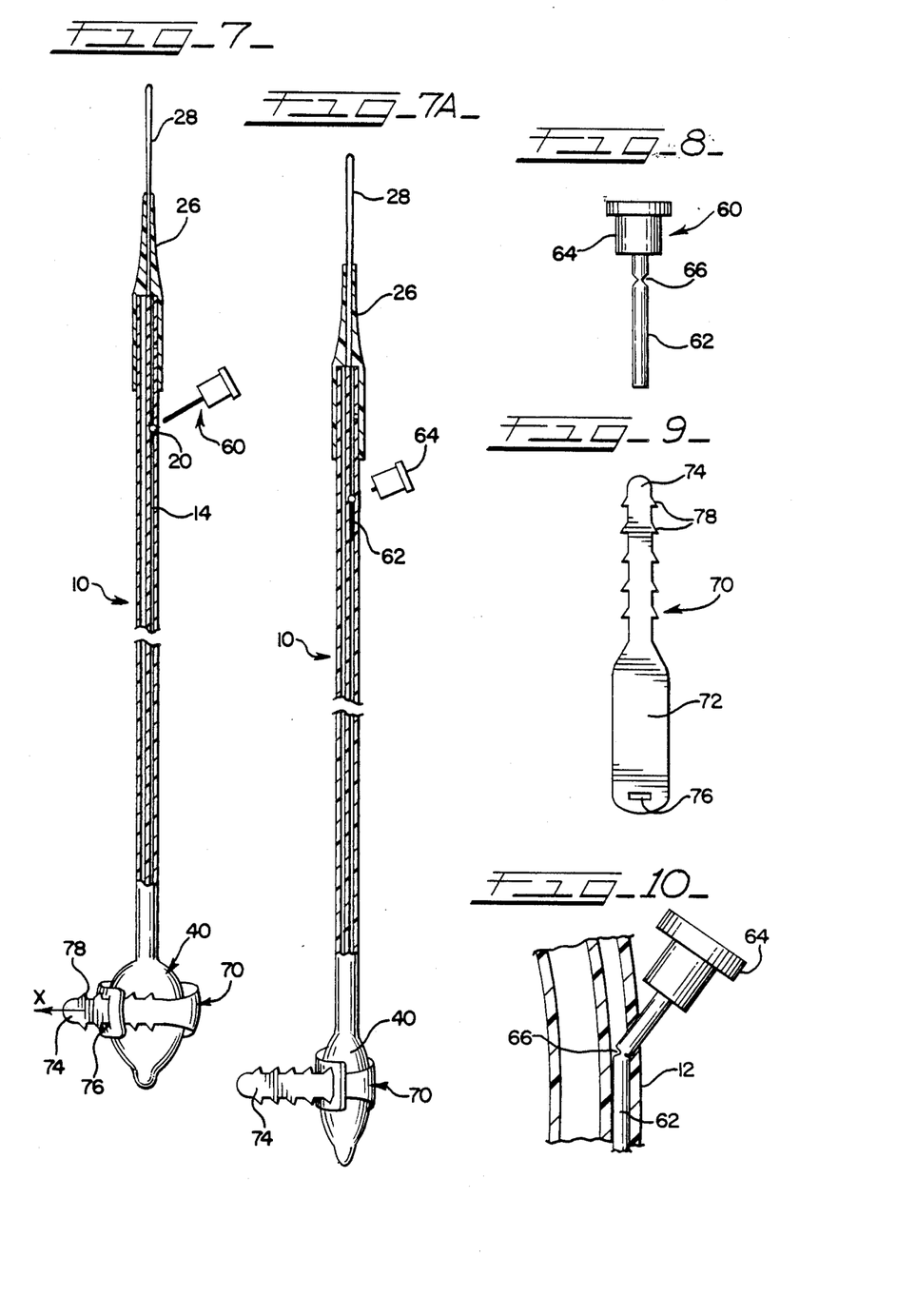
FIG. 7 is a partial longitudinal section disclosing an alternate embodiment of the present invention.
FIG. 7A is the same view of FIG. 7 wherein a plug member having a frangible stem seals the inflation lumen.
FIG. 8 is a side elevational view disclosing an embodiment of a frangible plug member.
FIG. 9 is a plan view of an open and extended embodiment of an deflation strap.
FIG. 10 is a detailed longitudinal section of a portion of a multi-lumen tube disclosing the frangible plug member of FIG. 8 occluding the inflation lumen.

As best disclosed in FIGS. 7 and 7A a multilumen enteral feeding tube 10 as previously disclosed is provided wherein skirt 36 is omitted or rendered non-functional. However, in this embodiment, tapered end 26 is nonetheless utilized to facilitate intubation. In this embodiment, ambient-air port 20 is exposed rather than being concealed underneath skirt 36. In this embodiment, initial sealing of the inflation lumen 14 is accomplished by occluding the lumen with a plug member of the type disclosed in FIG. 8 which is inserted into the lumen through ambient-air port 20.

As disclosed in FIG. 8, frangible plug 60 generally comprises a solid cylindrical stem 62 and an enlarged gripping portion 64 on one end of stem 62. A portion of stem 62 is crimped or narrowed to define a frangible region 66. The diameter of stem 62 is dimensioned to permit an interference fit with the inner diameter of inflation lumen 14. Frangible region 66 is adapted to allow gripping portion 64 to be twisted or bent to break-off stem 62 allowing the gripping portion to be removed.

As disclosed in FIGS. 7 and 7A, prior to intubation, retention member 40 is compressed. In this embodiment, however, inflation lumen 14 is occluded by inserting plug 60 into the inflation lumen while the member 40 is still compressed thus preventing premature re-inflation of the retention member.

FIG. 10 best discloses that the frangible plug 60 is inserted through ambient port 20 to a position where frangible portion 66 is inside inflation lumen 14 so that when stem 62 is broken from gripping portion 64, stem 62 is totally enclosed with lumen 14 thus not presenting any protrusion which would cause damage during intubation.

In this embodiment, retention member 40 may be compressed by squeezing the member in the palm off one hand while holding tube 12 between the thumb and forefinger of the same hand leaving the other hand of the user free to grip the frangible plug for insertion while the member remains compressed.

After intubation, air may be introduced into the retention member 40 in a manner similar to that disclosed above by cutting the multi-lumen tube 12 below the occluded area. As disclosed above the retention member may be maintained in the reinflated position by the insertion of another frangible plug member into the exposed open end of the inflation lumen 14.

Preferred embodiments of the invention provide for means to compress retention member 40 and maintain it in a compressed state until inflation lumen 14 can be occluded.

In one embodiment an adjustable strap 70 such as disclosed in FIG. 9 is provided. Strap 70 is a generally flat flexible member including a widened body portion 72, an integral narrowed tongue portion 74 on one end of the body portion which has a plurality of barbs 78 on the its edges and a slot 76 at an opposite end of the body portion. Body portion 72 is dimensioned to engage on a substantial portion of the outer surface of retention member 40. Tongue portion 74 is cooperatively dimensioned with slot 76 so that the tongue may be inserted into the slot and pulled therethrough with barbs 78 engaging the edges of the slot to prevent retrograde movement of the tongue.

Thus, as disclosed in FIGS. 7 and 7A, prior to intubation retention member 40 is captured within strap 70 and then the tongue 74 is pulled through slot 76 to compress the member and maintain the member in the compressed state until the user can insert frangible plug member 60 into port 20 to seal the inflation lumen 14. Once the plug member is inserted, strap 70 can be removed by pulling or cutting the strap.

Utilization of the compression strap allows the user to more easily accomplish retaining the member in a compressed state until the lumen can be plugged. More importantly, use of the compression strap provides an aseptic means for compressing the retention member by avoiding direct contact of the member by a user's hands.

Figure 11:
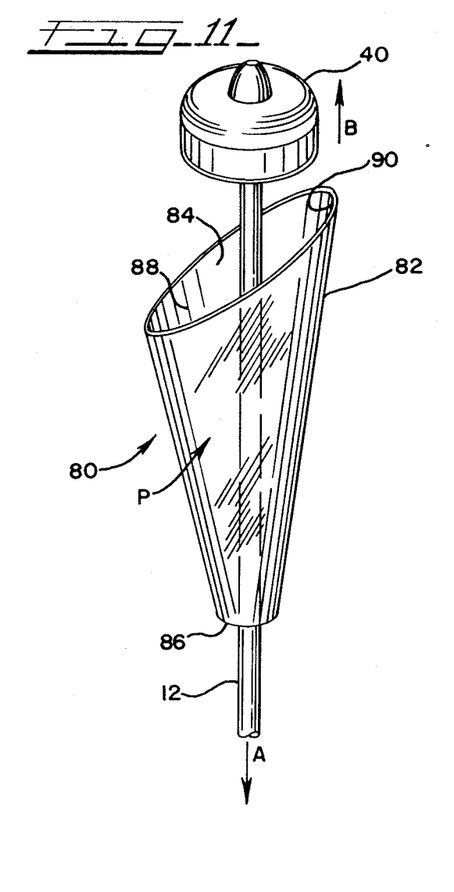
FIG. 11 is a side perspective view of a transparent deflation collar disposed on the multi-lumen feeding tube proximate to an inflated retention member.
Figure 12:
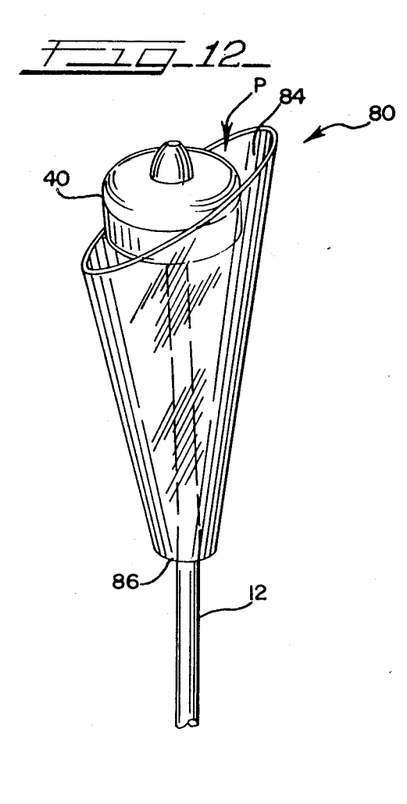
FIG. 12 discloses the view of FIG. 11 but with the retention member residing in a first open end of the deflation collar; and, FIG. 13. discloses the view of FIG. 11 but with the retention member advanced to a second open end of the deflation collar.
Figure 13:
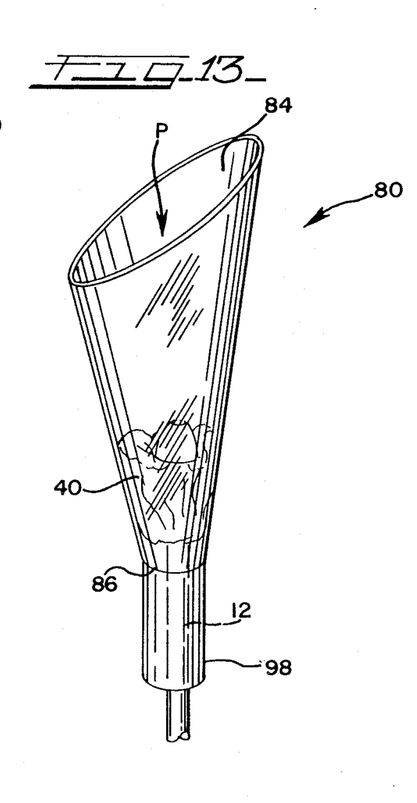

In an alternate embodiment of the invention a deflation collar 80 is provided to deflate the retention member 40 as disclosed in FIGS. 11 through 13. The deflation collar 80 has a continuous generally tubular wall 82. Wall 82 defines a passage P which interconnects first and second collar openings 84 and 86 respectively at opposed ends thereof. The first collar opening 84 is dimensioned to receive the retention member 40 therein when the member is fully inflated. The second collar opening 86 is dimensioned to permit the member 40 to reside therein or pass therethrough only when the member 40 has been substantially deflated. The tubular wall 82, and thus passage P, tapers from the first collar opening 84 to the second collar opening 86.

The tube 12 is disposed through the passage P. Preferably, the retention member 40 resides in the deflation collar 80 near the first collar opening 84 when the unit is stored prior to intubation as shown in FIG. 12. Thus the deflation collar helps to keep the retention member free from soiling.

When the device of the invention is ready for use, the retention member 40 is urged further into the deflation collar toward the second collar opening 86. This is accomplished by pulling the tube 12 in the direction of the arrow A in FIG. 11 and pulling the deflation collar in the opposite direction as indicated by arrow B. This action draws the retention member 40 through passage P. As the retention member 40 progresses, it is compressed by the tapered tubular wall 82 as shown in FIGS. 12 and 13. Preferably, when the retention member 40 has reached the second collar opening 86 it has been fully deflated as shown in FIG. 13. At this point, the inflation lumen 14 can be occluded to prevent the retention member 40 from re-inflating. The retention member 40 can then be pulled through the second collar opening 86 to remove deflation member 80 at any time desired before the intubation.

Utilization of this embodiment of the invention is particularly useful when the desired length of the tube 12 is on the order of 42 inches. With that length of tube 12, the loop 28 can be intubated and pulled through the gastrostomy without retention member 40 entering the body. In that case, retention member 40 may remain unattended because of the aseptic protection provided by the deflation collar 80.

Preferably, the periphery of the first collar opening 84 is biased with respect to the axis of the tubular wall 82. This provides an elongated shape to the first collar opening 84 and thus a space 88 and a tab 90 are defined when the retention member 40 resides therein as shown in FIG. 12. The tab 90 can be utilized to pull the deflation collar in an opposite direction of the tube 12 when deflating the retention member 40. The space 88 can be utilized for accessing the interior of the deflation collar wall 82 to apply a lubricant to aid in the pulling of the retention member 40 therethrough. Preferably, the deflation collar 80 is made from a resilient substantially transparent material so that the retention member 40 can be observed as it progresses therethrough. In the event a resilient material is used, the second collar opening 86 and a portion of the passage P proximate thereto can be dimensionally reduced so that the retention member in its deflated condition is resiliently retained when residing therein.

A flange such as cylindrical flange 98 shown in FIG. 13 can extend from the second collar opening 86. Flange 98 provides for added securement of the retention member 40 in the deflated state when the member 40 is to be left unattended.

While the specific embodiments have been illustrated and described, numerous modifications come to mind without significantly departing from the spirit of the invention and the scope of protection is only limited by the scope of the accompanying claims.

We claim:

1. A device for intubating an ostomy, such as a gastrostomy, comprising:

a tube having at least a fluid lumen and an inflation lumen, the tube having a port near one end to dispose the inflation lumen to ambient air and an outlet at an other end to convey fluid from within the fluid lumen into the patient;

a retention member joined near the other end of the tube, the member being inflatable through the inflation lumen, the member in a deflated state having decreased outer dimensions to facilitate intubation, the member in an inflated state having increased outer dimensions to facilitate retention and anchoring of the device within a patient;

a tapered sleeve joined to and sealing the one end of the tube; and means for sealing the ambient air port of the tube;

wherein prior to intubation, the retention member is compressed to deflate the member by expelling air out of the inflation lumen through the port, the sealing means is used to seal the port to prevent re-inflation of the member, the one end of the tube is drawn through the patient in a retrograde manner until the deflated retention member abuts against inner tissue surfaces of the ostomy, air is introduced into the inflation lumen to re-inflate the member and anchor the device against the inner tissue surfaces of the ostomy, and the sealing means re-seals the inflation lumen to prevent deflation of the retention member.

2. The device of claim 1 wherein the retention member includes a pre-distended inflatable balloon.

3. The device of claim 1 wherein the retention member includes a substantially foam-filled annular cuff.

4. The device of claim 1 further including means for deflating the retention member comprising:

a deflation collar having opposed first and second collar openings therein and a passage interconnecting the collar openings;

the first collar opening being dimensioned to permit the retention member to reside therein in an inflated state;

the second collar opening being dimensioned to allow passage of the retention member therethrough only when the retention member is in a substantially deflated state; and, the passage being tapered from the first collar opening to the second collar opening so that, as the retention member is urged through the deflation collar from the first collar opening to the second collar opening, the retention member will be deflated.

5. The device of claim 4 wherein the deflation collar is made from a resilient material.

6. The device of claim 5 wherein the second collar opening and a portion of the passage proximate thereto are dimensioned so that the they are resiliently urged against the retention member as it resides therein or passes therethrough.

7. The device of claims 4, 5 or 6 wherein the first collar opening is shaped so that interior surfaces of the deflation collar can be accessed for lubrication thereof when the fully inflated retention member is residing in the first collar opening.

8. A device for asepticly deflating an inflatable retention member carried on an apparatus for intubating an ostomy, such as a gastrostomy, formed by a percutaneous endoscopic technique, comprising:

a deflation collar having opposed first and second collar openings therein and a passage interconnecting the first and second collar openings;

the first collar opening being dimensioned to permit the retention member to reside therein in an inflated state;

the second collar opening being dimensioned to allow passage of the retention member therethrough only when the retention member is in a substantially deflated state;

the passage being tapered from the first collar opening to the second collar opening so that, as the retention member is urged through the deflation collar from the first collar opening to the second collar opening, the retention member will be deflated.

9. The device of claim 8 wherein the first collar opening is shaped so that interior surfaces of the deflation collar can be accessed for lubrication thereof when the fully inflated retention member is residing in the first collar opening.

10. The device of claim 8 wherein a periphery of the first collar opening is biased with respect to an axis of the passage so that interior surfaces of the deflation collar can be accessed for lubrication thereof when the fully inflated retention member is residing in the first collar opening and so that a tab is defined along a portion of the periphery of the opening.

11. The device of claims 8, 9 or 10 wherein at least a portion of the tube is disposed through the passage prior to deflation of the retention member.

12. In a method for intubating an ostomy formed by a percutaneous endoscopic technique, the technique including inserting an endoscope into a patient's mouth, advancing the endoscope into the patient to illuminate and externally visualize a desired endoscope positioning, forming the ostomy through abdominal and gastric walls of the patient at the desired endoscope positioning, and passing one end of a suture externally through the ostomy and drawing the one end of the suture up through and out of the patient's mouth, an other end of the suture remaining outside the gastrostomy, the improvement comprising the steps of:

tying the suture to one end of a tube having at least an inflation lumen and a fluid lumen, the tube having a port near the one end to dispose the inflation lumen to ambient air and an outlet at an other end to convey fluid from the fluid lumen into the patient, an elongated tapered sleeve joined to and sealing the one end of the tube;

urging an inflatable retention member joined near the other end of the tube through a small end of a deflation collar having a tapered passage;

allowing the retention member to reside in the passage until the inflation lumen has been sealed;

sealing the inflation lumen to prevent re-inflation of the retention member;

removing the deflation collar from the retention member;

intubating the tube by pulling on the other end of the suture to draw and lead the one end of the tube in a retrograde manner through the patient until the retention member abuts against inner tissue surfaces of the ostomy; and, re-inflating the retention member to anchor the member against the inner tissue surfaces of the ostomy.

13. The method of claim 12 wherein the step of urging comprises:

securing the deflation collar; and, drawing the retention member into the small end of the tapered passage of the deflation collar by pulling the tube attached to the retention member.

* * * * *

UNITED STATES PATENT AND TRADEMARK OFFICE
CERTIFICATE OF CORRECTION

PATENT NO. : 4,981,471

DATED : January 1, 1991

INVENTOR(S) : David G. Quinn, Robert B. Edwards II and Erik Andersen

It is certified that error appears in the above-identified patent and that said Letters Patent is hereby corrected as shown below:

In Column 5, line 13, delete "an" and insert therefor --a--.

In Column 5, line 56, delete "a traumatic and insert therefor --atraumatic--.

In Column 6, line 4, delete "and" and insert therefor --end--.

In Column 7, line 11, delete the second "a" and insert therefor --an--.

In Column 8, line 14, delete "multilumen" and insert therefor --multi-lumen--.

In Column 8, line 49, delete "off" and insert therefor --of--.

In Column 9, line 2, delete the first "the".

Signed and Sealed this

Twenty-eighth Day of July, 1992

Attest:

DOUGLAS B. COMER

Attesting Officer     Acting Commissioner of Patents and Trademarks